United States Patent [19]

Kohler

[11] 4,183,880
[45] Jan. 15, 1980

[54] PREPARATION OF O,O-DIALKYL-S-(N-METHYLCARBOX-AMIDOMETHYL)-THIOLPHOSPHORIC ACID ESTERS

[75] Inventor: Egon Kohler, Dormagen, Fed. Rep. of Germany

[73] Assignee: Bayer Aktiengesellschaft, Dormagen, Fed. Rep. of Germany

[21] Appl. No.: 856,456

[22] Filed: Nov. 30, 1977

[30] Foreign Application Priority Data

Dec. 9, 1976 [DE] Fed. Rep. of Germany ....... 2655823

[51] Int. Cl.² ............................................. C07F 9/165
[52] U.S. Cl. ..................................................... 260/970
[58] Field of Search .................................. 260/970, 45

[56] References Cited

U.S. PATENT DOCUMENTS 3,156,718  11/1964  Lorenz et al. ..................... 260/970

FOREIGN PATENT DOCUMENTS 1144265  2/1963  Fed. Rep. of Germany ........... 260/943

OTHER PUBLICATIONS

Pudovik et al, "J. Gen. Chem. U.S.S.R.," vol. 23, (1953), English translation, pp. 273–276.
Abramov et al, "J. Gen. Chem. U.S.S.R.," vol. 23, (1953), English translation, pp. 1061–1065.

*Primary Examiner*—Anton H. Sutto
*Attorney, Agent, or Firm*—Sprung, Felfe, Horn, Lynch & Kramer

[57] ABSTRACT

A process for the preparation of an O,O-dialkyl-S-(N-methylcarboxamidomethyl)-thiolphosphoric acid ester of the formula

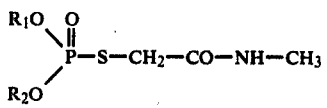

in which
R$_1$ and R$_2$ each independently is alkyl, comprising reacting a salt of N-methylcarboxamidomethyl-thiosulphuric acid with an O,O-dialkyl phosphorous acid of the formula

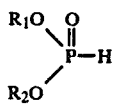

in a suspension in the presence of an alkaline earth metal alcoholate, alkali metal carbonate or alkaline earth metal carbonate, e.g. magnesium methylate or ethylate, calcium methylate or ethylate, potassium carbonate, sodium carbonate, magnesium carbonate or calcium carbonate. Advantageously R$_1$ and R$_2$ each independently has up to 4 carbon atoms, the N-methylcarboxamidomethyl-thiosulphuric acid salt is an alkali metal salt and the reaction is carried out in ethylene chloride or chloroform at a temperature of about 10° to 40° C. in the presence of triethylamine as catalyst.

9 Claims, No Drawings

PREPARATION OF O,O-DIALKYL-S-(N-METHYLCARBOX-AMIDOMETHYL)-THIOLPHOSPHORIC ACID ESTERS

The present invention relates to an unobvious process for the preparation of certain O,O-dialkyl-S-(N-methylcarboxamidomethyl)-thiolphosphoric acid esters which, as is known, may be used as insecticides.

A large number of processes for the preparation of the above-mentioned thiolphosphoric acid esters are already known from the literature, such as the reaction of alkali metal salts of O,O-dialkyl-thiophosphoric acids with a halogenoacetic acid methylamide (see German Patent Specification 819,998), and also the reaction of O,O-dialkyl-thiolphosphorylacetic acid with methyl isocyanate (German Patent Specification 1,251,304).

Furthermore, the preparation of thiolphosphoric, thiolphosphonic and thiolphosphinic acid esters and the corresponding dithio compounds by reacting the salts of thiosulphuric acid monoesters (BUNTE salts) with salts of O,O-dialkyl phosphorous or O,O-dialkyl-thiolphosphorous acid esters, phosphonous or thiolphosphonous acid esters or phosphinous or thiolphosphinous acids has also already been described (see German Patent Specifications 1,240,034 and 1,144,265).

However, all the above-mentioned known processes have a number of considerable disadvantages.

Thus, for example, the yield in the reaction of potassium O,O-dimethylthiolphosphate and chloroacetic acid methylamide according to German Patent Specification 819,998 is only 34% of theory, and in addition the product obtained decomposes very rapidly during storage, in particular at a slightly elevated temperature. The product of the reaction of O,O-dimethylthiolphosphorylacetic acid and methyl isocyanate according to German Patent Specification 1,251,304 leaves much to be desired with regard to its content of the desired active compound and with respect to the heat stability. Finally, the processes according to German Patent Specifications 1,144,265 and 1,124,034 are also characterized by the disadvantage of poor yields and an inadequate quality of the product, in particular as far as the preparation of the thiolphosphoric acid esters, which alone are of interest here, is concerned.

The present invention provides a process for the preparation of an O,O-dialkyl-S-(N-methyl-carboxamidomethyl)thiolphosphoric acid ester of the general formula

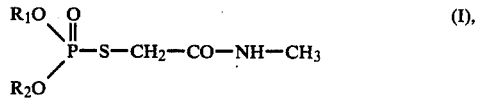

in which
R$_1$ and R$_2$ represent identical or different alkyl radicals,
in which a salt of N-methylcarboxamidomethylthiosulphuric acid is reacted with an O,O-dialkylphosphorous acid, the reaction being carried out in a suspension in the presence of an alkaline earth metal alcoholate, alkali metal carbonate or alkaline earth metal carbonate, preferably in the presence of an organic base as a catalyst, and preferably using a non-polar solvent or diluent.

Preferably, R and R$_1$ represent identical or different, straight-chain or branched alkyl radicals with up to 4, especially 1 or 2, carbon atoms, and most preferably they each represent methyl.

The smooth and uniform course of the reaction in the process according to the invention is exceptionally surprising and could in no way be predicted, since, according to the procedure described in German Patent Specifications 1,124,034 and 1,144,265, thiolphosphoric acid esters of the type under discussion (in contrast to the corresponding dithio- or thiono-phosphoric acid esters) either cannot be obtained at all or can be obtained only in a highly impure form and in extremely poor yields by reacting salts of thiosulphuric acid monoesters with salts of O,O-dialkylphosphorous acids under the reaction conditions indicated therein, since both the starting materials and the end products are subject to a saponification that proceeds as a competing reaction, thiolphosphoric acid esters of the type under discussion, as is known, being particularly rapidly saponified. Thus, according to Example 8 of German Patent Specification 1,144,265, O,O-dimethyl-S-(N-methylcarboxamidomethyl)-thiolphosphoric acid ester is obtained only in the form of a colorless viscous water-insoluble oil, while it is known from the literature, on the other hand, that the above-mentioned product is distinguished by a particularly good solubility in water and organic solvents.

Compared with the state of the art, the process according to the invention has a number of significant advantages. There should be mentioned, in particular, the possibility of carrying out the reaction in suspension, preferably also using non-polar diluents, by which means the saponification reaction can be substantially eliminated. The water required for the reaction is present in the BUNTE salt, to be used as the starting material, in the form of water of crystallization which is released only temporarily during the reaction, that is to say is immediately bonded again by the alkali metal sulphites or carbonates or alkaline earth metal sulphites or carbonates formed as by-products.

Furthermore, the thiolphosphoric acid esters which can be prepared by the process according to the invention, in contrast to the products obtained according to the state of the art, are distinguished by a substantially increased heat stability. Thus, for example, the O,O-dimethyl-S-(N-methylcarboxamidomethyl)-thiolphosphoric acid ester obtainable according to German Patent Specification 1,144,265, in comparison to the corresponding dithio compound, has a considerably poorer resistance to heat. In contrast to this, the product obtainable by the "suspension-BUNTE salt reaction" in the process according to the invention, compared to the dithiophosphoric acid ester of an analogous structure, has proved to be about 2.5 times more stable in 50° C. storage experiments.

If, for example, O,O-dimethylphosphorous acid, sodium N-methylcarboxyamidomethylthiosulphate and calcium methylate or potassium carbonate are used as the starting materials, the course of the reaction can be represented by the following equations.

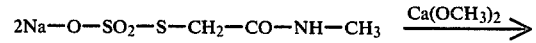

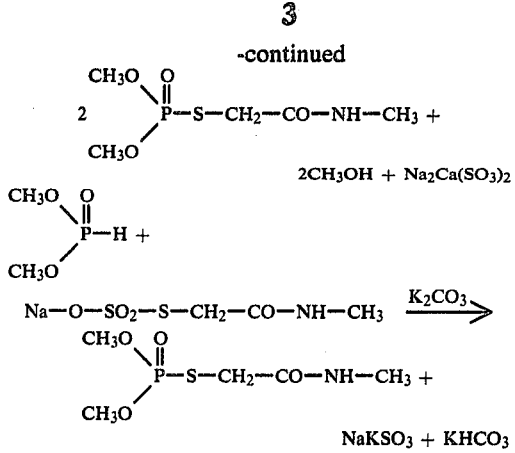

$$\text{NaKSO}_3 + \text{KHCO}_3$$

Examples which may be mentioned of O,O-dialkylphosphorous acids to be reacted in the present process are O,O-dimethylphosphorous acid and O,O-diethylphosphorous acid.

The salts of N-methylcarboxamidomethyl-thiosulphuric acid which are also required as starting materials are known from the literature and are also readily available on an industrial scale by reacting an alkali metal thiosulphate, preferably sodium thiosulphate, with a halogenoacetic acid methylamide, preferably chloroacetic acid methylamide.

As already mentioned briefly above, the process according to the invention is preferably carried out in the presence of a non-polar solvent or diluent. Preferred nonpolar solvents or diluents which can be used are chlorinated hydrocarbons, for example methylene chloride, ethylene chloride, chloroform or carbon tetrachloride.

Acid-binding agents which are used are, preferably, magnesium methylate or ethylate or calcium methylate or ethylate, and also sodium carbonate, potassium carbonate, magnesium carbonate or calcium carbonate.

Moreover, the reaction according to the invention is preferably carried out in the presence of a nitrogen-containing organic base, in particular triethylamine, as a catalyst.

The process according to the invention can be carried out within a wide temperature range. In general, the reaction is effected at about 0° to +80° C., preferably at about 10° to 40° C.

As already mentioned, the thiolphosphoric acid esters obtainable according to the process are known, valuable, insecticidally active compounds which are used as agents for combating pests, in particular in plant protection.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperature and pressures, such as halogenated hydrocarbons, e.g. dichlorodifluoromethane and trichlorofluoromethane, as well as butane, propane, nitrogen and carbon dioxide; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylene, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethylsulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as nonionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl or polyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other insecticides, acaricides, nematocides, bactericides and fungicides, or rodenticides, herbicides, fertilizers, growth-regulating agents, bird repellents, plant nutrients, agents for improving soil structure, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.000000–100, preferably 0.01–10% by weight of the mixture. Thus, the present invention contemplates overall compositions which comprise mixtures of a conventional dispersible carrier vehicle such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.000000–95% and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the active compounds of the present invention can be used for selectively killing, combating or controlling pests, e.g. insects, by applying to at least one of correspondingly (a) such insects, and (b) the corresponding habitat thereof, i.e. the locus to be protected, e.g. to a growing crop, to an area where a crop is to be grown or to a domestic animal, a correspondingly combative or toxic amount, i.e. an insecticidally effective amount, of the particular active compound of the invention alone or together with a carrier vehicle as noted above. The formulations or compositions are applied in the usual manner, for instance by spraying, atomizing, vaporizing, scattering, dusting, watering, squirting, sprinkling, pouring, fumigating, dry dressing, moist dressing, wet dressing, slurry dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The following preparative examples illustrate the process according to the invention.

EXAMPLE 1

(a) The salts of N-methylcarboxamidomethyl-thiosulphuric acid required as starting materials could be prepared, for example, as follows:

Na—O—SO$_2$—S—CH$_2$—CO—NH—CH$_3$

To 277 ml of a 40% strength sodium thiosulphate melt in a 1-liter round-necked flask were added at 40° C. 100 g of monochloroacetic acid N-monomethylamide (softening point 45° C.) dropwise from a heated dropping funnel in the course of 10 minutes. During this addition, the reaction temperature rose to 60° C. and was kept at this value for 3 hours. The mixture was then cooled to +10° C. and the crystals which had precipitated were filtered off. The latter were dried in air. The crude yield was 215 g, corresponding to 208 g of 100% pure sodium N-methylcarboxamidomethyl-thiosulphate (92.1% of theory).

The crude product contained small amounts of sodium chloride as an impurity, which could be separated off by recrystallization from methanol. The pure product (BUNTE salt) crystallized in the form of fine white needles with a melting point of 95° to 96° C.

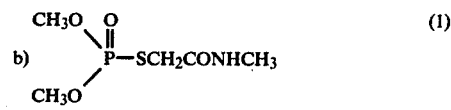

121.5 g (0.5 mol) of sodium N-methylcarboxamidomethyl-thiosulphate (BUNTE salt) were mixed together with 80 g of O,O-dimethyl-phosphorous acid and 1 ml of triethylamine to give a slurry which could be stirred. 311 g of a 12.6% strength methanolic calcium methylate suspension were added in 3 portions to this mixture in the course of 15 minutes. The reaction temperature was kept at room temperature by external cooling by means of ice-water. The mixture was subsequently stirred for one hour and the methanol was then substantially distilled off under reduced pressure at 35° C. The suspension which remained was substantially dissolved by adding 300 ml of water and 200 ml of chloroform and the insoluble salt-like constituent was filtered off and washed with a little chloroform. After separating the aqueous and organic layer, the former was extracted five times with 100 ml of chloroform each time. The combined chloroform solutions were dried over sodium sulphate. After distilling off the solvent under reduced pressure, O,O-dimethyl-S-(N-methylcarboxamidomethyl)-thiolphosphoric acid ester remained in the form of a water-clear liquid which was outstandingly soluble in almost all organic solvents and in water. The yield was 68 g and the content of pure active compound in the end product was 95%, corresponding to a yield of 100% pure product of 60.6% of theory.

EXAMPLE 2

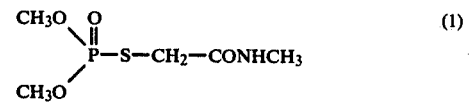

121.5 g (0.5 mol) of sodium N-methylcarboxamidomethyl-thiosulphate were mixed together with 70 g of O,O-dimethyl phosphorous acid and 1 ml of triethylamine to give a slurry which could be stirred. A total of 188 g of a 17.1% strength methanolic magnesium methylate suspension were then added in 3 portions to the latter in the course of 15 minutes at room temperature, externally cooling with ice. The reaction mixture was subsequently stirred for one hour, the methanol was then distilled off under reduced pressure at 35° C. and the suspension which remained was substantially brought into solution by adding 300 ml of water and 200 ml of chloroform. The insoluble salt-like constituents were filtered off and washed with a little chloroform. The aqueous phase was then extracted with chloroform. Finally, the combined chloroform phases were dried over sodium sulphate. After distilling off the solvent under reduced pressure, 59.5 g (51.9% of theory) of O,O-dimethyl-S-(N-methylcarboxamidomethyl)-thiolphosphoric acid ester with a content of active compound of 94.5% were obtained.

EXAMPLE 3

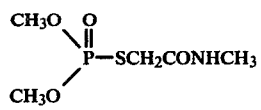
(1)

121.5 g (0.5 mol) of sodium N-methylcarboxamidomethyl-thiosulphate were suspended, with the addition of 0.2 ml of triethylamine and 70 g of O,O-dimethyl-phosphorous acid, in 200 ml of ethylene chloride. 96.5 g of potassium carbonate (0.5 mol+40% excess) were rapidly introduced into this suspension, while intensively cooling externally. The reaction temperature rose to 40° C. and was kept at this value for 5 hours. The crystals which had separated out were then filtered off and washed with 200 ml of ethylene chloride. The ethylene chloride solution was then dried over sodium sulphate and concentrated as far as possible under reduced pressure. 98 g (90.3% of theory) of O,O-dimethyl-S-(N-methylcarboxyamidomethyl)-thiolphosphoric acid ester with a content of active compound of 98.1% remained.

EXAMPLE 4

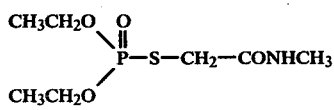
(2)

121.5 g (0.5 mol) of sodium N-methylcarboxamidomethyl-thiosulphate were suspended, together with 0.2 ml of triethylamine and 88 g of O,O-diethyl-phosphorous acid, in 200 ml of ethylene chloride and 96.5 g of potassium carbonate (0.5 mol+40% excess) were introduced rapidly into this suspension, while intensively cooling externally. During this procedure, the temperature of the mixture rose to 40° C. and was kept at this value for 5 hours. The crystals which had separated out were then filtered off and washed with 200 ml of ethylene chloride. Finally, the ethylene chloride solution was dried over sodium sulphate and concentrated as far as possible under reduced pressure. 111.5 g (91.8% of theory) of O,O-diethyl-S-(N-methyl-carboxamidomethyl-thiolphosphoric acid ester remained in the form of a water-clear liquid.

The content of active compound was 99.0%.

It will be appreciated that the instant specification and examples are set forth by way of illustration and not limitation, and that various modifications and changes may be made without departing from the spirit and scope of the present invention.

What is claimed is:
1. A process for the preparation of an O,O-dialkyl-S-(N-methyl-carboxamidomethyl)-thiolphosphoric acid ester of the formula

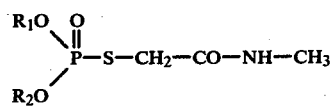

in which
R$_1$ and R$_2$ each independently is alkyl, comprising reacting a salt of N-methylcarboxamidomethyl-thiosulphuric acid with an O,O-dialkyl phosphorous acid of the formula

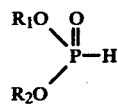

in a suspension in a non-polar solvent in the presence of an alkali metal carbonate or alkaline earth metal carbonate.

2. A process according to claim 1, in which the reaction is carried out in the presence of a nitrogen-containing organic base as a catalyst.

3. A process according to claim 2, in which the nitrogen-containing base is triethylamine.

4. A process according to claim 1, in which a chlorinated hydrocarbon is used as the non-polar solvent or diluent.

5. A process according to claim 4, in which the chlorinated hydrocarbon is ethylene chloride or chloroform.

6. A process according to claim 1, in which the reaction is carried out in the presence of potassium carbonate, sodium carbonate, magnesium carbonate or calcium carbonate.

7. A process according to claim 1, in which the reaction is effected at about 0° to +80° C.

8. A process according to claim 6, in which R$_1$ and R$_2$ each independently has up to 4 carbon atoms, the N-methylcarboxamidomethyl-thiosulphuric acid salt is an alkali metal salt, and the reaction is carried out in ethylene chloride or chloroform at a temperature of about 10° to 40° C. in the presence of triethylamine as catalyst.

9. A process according to claim 8, in which the salt of N-methylcarboxamidomethyl-thiosulphuric acid and the O,O-dialkyl phosphorous acid are first combined in ethylene chloride or chloroform and the carbonate is thereafter added.